(12) United States Patent
Weil et al.

(10) Patent No.: US 7,445,650 B2
(45) Date of Patent: Nov. 4, 2008

(54) CONTROL OF PRESSURIZED MICROCHANNEL PROCESSES

(75) Inventors: Christopher P. Weil, Pickerington, OH (US); Robert D. Litt, Westerville, OH (US); William Allen Rogers, Jr., Marysville, OH (US); Richard K. Bennett, Mansfield, OH (US); Elizabeth A. De Lucia, Columbus, OH (US)

(73) Assignee: Velocys, Inc., Plain City, OH (US)

( * ) Notice: Subject to any disclaimer, the term of this patent is extended or adjusted under 35 U.S.C. 154(b) by 729 days.

(21) Appl. No.: 11/077,849

(22) Filed: Mar. 11, 2005

(65) Prior Publication Data

US 2005/0214202 A1    Sep. 29, 2005

Related U.S. Application Data

(63) Continuation-in-part of application No. 10/774,298, filed on Feb. 6, 2004.

(51) Int. Cl.
*C01B 3/24* (2006.01)
*C01B 3/36* (2006.01)
*C01B 3/02* (2006.01)
*B01L 3/00* (2006.01)
*F01N 3/20* (2006.01)

(52) U.S. Cl. ............ 48/198.1; 48/197 R; 48/198.7; 422/102; 422/105; 422/130; 422/198; 423/648.1; 423/650; 423/651

(58) Field of Classification Search .......... 48/197 R, 48/198.1, 198.7; 422/102, 105; 423/648.1, 423/650, 651
See application file for complete search history.

(56) References Cited

U.S. PATENT DOCUMENTS

2,462,517 A    2/1949    Leverenz (Continued)

FOREIGN PATENT DOCUMENTS

EP    1 400 280 A1    3/2004

(Continued)

OTHER PUBLICATIONS

Driscol, et al., 300 MWe Supercritical CO2 Plant Layout and Design, Topical Report, Report No. MIT-GFR-014, Jun. 2004, Center for Advanced Nuclear Energy Systems, MIT Nuclear Engineering Department, Cambridge, MA, USA.

(Continued)

*Primary Examiner*—Walter D. Griffin
*Assistant Examiner*—Lessanework T Seifu
(74) *Attorney, Agent, or Firm*—William B. Richards, Esq.; The Richards Law Firm (57) ABSTRACT

A method of starting up and shutting down a microchannel process is provided. Included are the steps of providing a first multi-planar process unit, preferably adapted to process an endothermic reaction, a second multi-planar process unit, preferably adapted to process an exothermic reaction, providing a containment vessel, the containment vessel containing at least a portion of the first, and preferably the second, process unit. In startup, the microchannel process is first checked for pressure integrity by pressurizing and checking the important components of the process for leaks. Subsequently, the process units are heated by introducing a dilute low-thermal energy density material, preferably to the second process unit, followed by the introduction of a dilute high-thermal energy density material, and adjusting the proportion of high-thermal energy density material as required. In shutdown, a purge material from the containment vessel is introduced into the first, and preferably the second, process unit.

63 Claims, 6 Drawing Sheets

U.S. PATENT DOCUMENTS

| | | | |
|---|---|---|---|
| 2,997,435 A | | 8/1961 | Miller et al. |
| 3,515,520 A | | 6/1970 | Hervert |
| 4,167,915 A | | 9/1979 | Toole et al. |
| 4,232,179 A | | 11/1980 | Valladares Barrocas et al. |
| 4,253,417 A | | 3/1981 | Valentijn |
| 4,670,404 A | | 6/1987 | Swift et al. |
| 5,167,930 A | | 12/1992 | Fassbender |
| 5,611,214 A | * | 3/1997 | Wegeng et al. ............. 62/498 |
| 5,811,062 A | * | 9/1998 | Wegeng et al. ............ 422/129 |
| 5,932,182 A | | 8/1999 | Blaney |
| 6,126,723 A | | 10/2000 | Drost et al. |
| 6,136,171 A | | 10/2000 | Frazier et al. |
| 6,159,434 A | | 12/2000 | Gonjo et al. |
| 6,192,596 B1 | | 2/2001 | Bennett et al. |
| 6,200,536 B1 | | 3/2001 | Tonkovich et al. |
| 7,118,917 B2 | | 10/2006 | Bergh et al. |
| 7,234,514 B2 | | 6/2007 | Vogel |
| 2002/0182735 A1 | | 12/2002 | Kibby et al. |
| 2004/0136902 A1 | | 7/2004 | Plath et al. |
| 2005/0025677 A1 | | 2/2005 | Oberbeck et al. |

FOREIGN PATENT DOCUMENTS

| | | | |
|---|---|---|---|
| GB | 2 128 013 A | | 4/1984 |
| WO | WO 2004/054013 A2 | | 6/2004 |

OTHER PUBLICATIONS

Freemantle, Michael, Microprocessing on a Large Scale, Chemical & Engineering News, Oct. 11, 2004, CR 2004, pp. 39-43, vol. 82, No. 41, American Chemical Society, USA.

Thayer, Ann M., Harnessing Microreactions, Chemical & Engineering News, May 30, 2005, CR 2005, pp. 43-52, vol. 83, No. 22, American Chemical Society, USA.

Wang, et al., Intensification of Gas-to-Liquid (GTL) Process Using Microchannel Technology, May 5, 2003, Pacific Northwest National Laboratory, Richland, WA and Velocys, Inc. Columbus, OH, USA.

Merkling, U.S. Appl. No. 10/774,298, USPTO OA, filed Jan. 30, 2008.

Merkling, U.S. Appl. No. 10/774,298, USPTO OA, filed Jun. 16, 2008.

Merkling, U.S. Appl. No. 10/774,298, USPTO OA, filed Aug. 9, 2007.

Young, U.S. Appl. No. 11/052,455, USPTO OA, filed Jul. 28, 2008.

Young, U.S. Appl. No. 11/052,455, USPTO OA, filed Dec. 27, 2007.

Leung, PCT/US05/03904 Written Opinion of the International Searching Authority May 17, 2005.

* cited by examiner

CONTROL OF PRESSURIZED MICROCHANNEL PROCESSES

CROSS-REFERENCE TO RELATED APPLICATION

This application claims priority to, and is a Continuation-in-Part of, application Ser. No. 10/774,298, filed Feb. 6, 2004, the contents of which, to the extent not inconsistent herewith, are incorporated herein by reference as if fully rewritten herein.

STATEMMENT REGARDING FEDERALLY-SPONSORED RESEARCH OR DEVELOPMENT

Not Applicable.

INCORPORATION-BY-REFERENCE OF MATERIAL SUBMITTED ON A COMPACT DISC

Not Applicable.

BACKGROUND OF THE INVENTION

1. Field of the Invention

The present invention is related to the control of microchannel processes, particularly microchannel processes which operate under generally high pressures and, optionally, generally high temperatures, and, more particularly, microchannel processes which comprise endothermic reactions such as steam methane reforming (SMR), and, optionally, exothermic reactions such as combustion. Control includes, particularly, methods of startup and shutdown of such processes.

2. Description of Related Art

Microchannel devices have demonstrated the capability of providing improved conversion of reactants to products as well as improved selectivity to desired products relative to undesired products and recent years have seen a significant increase in the application of microchannel processes to many unit operations. See, e.g., A. A. Rostami et al., *Flow and Heat Transfer for Gas Flowing In Microchannels: A Review*, 38 Heat and Mass Transfer 359-67 (2002) (applications in medicine, biotechnology, avionics, consumer electronics, telecommunications, metrology, and many others) and R. S. Wegeng et al., *Compact Fuel Processors for Fuel Cell Powered Automobiles Based on Microchannel Technology*, Fuel Cells Bulletin No. 28 (2002) (compact hydrogen generators for fuel cells). Microchannel processes utilize microchannel devices for carrying out unit operations that had previously been constrained to far larger equipment—often three to 1,000 times as large for comparable total throughput. Devices for microchannel processes, which microchannels contain features of at least one internal dimension of width or height of less than about 2 mm and preferably less than about 1 mm, have the potential to change unit operations in ways analogous to the changes that miniaturization has brought to computing technology. Microchannel processes can be used to advantage in small-scale operations, such as in vehicles or personal (portable) devices.

Importantly too, microchannel processes that can be economically mass-produced and connected together to accomplish large-scale operations are very desirable. For example, hydrogen gas is an important material in the operation of a petroleum refinery. The ability to economically generate hydrogen from a natural gas supply (i.e., methane) is important to such an operation and is typically effected, in part, via a reformer. In an SMR operation, for example, methane is catalytically reacted with water in the form of steam in the following reaction:

$$CH_4+H_2O \rightarrow 3H_2+CO.$$

SMR being an endothermic reaction, a combustion reactor is often combined with the reformer to provide the necessary thermal energy. Notably, the reformer is operated at a temperature of about 650-1,000 deg. C. and a pressure of about 300 psig. Many microchannel devices utilized for unit operations such as SMR include a multi-planar design which then must operate in the high temperature and pressure regimes noted. Unlike a tubular reactor, a multi-planar device does not easily handle such pressures at the temperatures required.

Although not exclusively, these process units are typically constructed by laminating multiple planar sheets together where some sheets comprise openings which cooperate with other sheets to form microchannels. See, e.g., Schmitt, "Method of Fabricating Multi-Channel Devices and Multi-Channel Devices Therefrom", U.S. Pat. No. 6,851,171 and Mathias et al., "Multi-Stream Microchannel Device", U.S. Pat. Pub. No. 2004/0031592 A1. In addition to the structural integrity issues raised by planar elements and laminations and the temperature and pressure issues noted above, thin walls to reduce weight and improve heat transfer add further complexity. This is even more evident during startup and shutdown (both normal and emergency and including shutdown and subsequent "hot startup") when temperature and pressure dynamics can be most difficult to control and which have the potential to damage the device or create hazardous conditions when flammable or potentially explosive mixtures are present. Thus, excess pressure differentials and uneven heating and "hot spots" in the device must be avoided or minimized.

BRIEF DESCRIPTION OF THE INVENTION

In accordance with the present invention, a method of starting up a microchannel process includes the steps of providing a first multi-planar process unit, providing a containment vessel at least partially containing the process unit, establishing a first containment vessel pressure within the containment vessel, sensing for leaks from the containment vessel, establishing a first process unit pressure within the first process unit, and sensing for leaks from the first process unit.

In a preferred embodiment, the method further includes the steps of providing a catalyst within the first process unit, providing a second multi-planar microchannel process unit, the second multi-planar microchannel process unit at least partially contained within the containment vessel, establishing a second containment vessel pressure within the containment vessel, checking for leaks from the containment vessel, initiating a first unit operation within the first process unit, initiating a second unit operation within the second process unit, and maintaining a differential between a containment vessel pressure and a first multi-planar microchannel process unit pressure, and, optionally, between the containment vessel pressure and a second multi-planar microchannel process unit pressure. More preferably, the first multi-planar microchannel process unit and the second multi-planar process unit are heated by introducing a stream to the second multi-planar process unit, the stream comprising a dilute low-thermal energy density material, decreasing the proportion of diluent in the stream (increasing the concentration of low-thermal energy density material), and replacing the low-thermal energy density material with a high-thermal energy density material. Thermal energy is transferred between the first process unit and the second process unit. Even more preferably, the first multi-planar microchannel process unit processes an SMR reaction and the second multi-planar microchannel process unit processes a combustion reaction.

In further accordance with the present invention, a method of starting up a microchannel process includes providing a microchannel process adapted to process a combustion operation, introducing a combustible compound and a diluent and an oxidizing compound to the process unit, initiating the combustion reaction, and decreasing the proportion of diluent. In a preferred embodiment, the method further includes providing a combustible compound comprising a low-thermal density material and replacing the low-thermal energy density material with a high-thermal energy density material.

In yet further accordance with the present invention, a method of shutting down a microchannel process includes providing a first microchannel process unit, discontinuing the flow of a first and a second reactant to the process unit, and introducing a fluid to the first process unit. In a preferred embodiment, the first microchannel process unit is at least partially contained within a containment vessel and the fluid is introduced from the containment vessel to the first process unit.

DETAILED DESCRIPTION OF THE INVENTION

Figure 1:
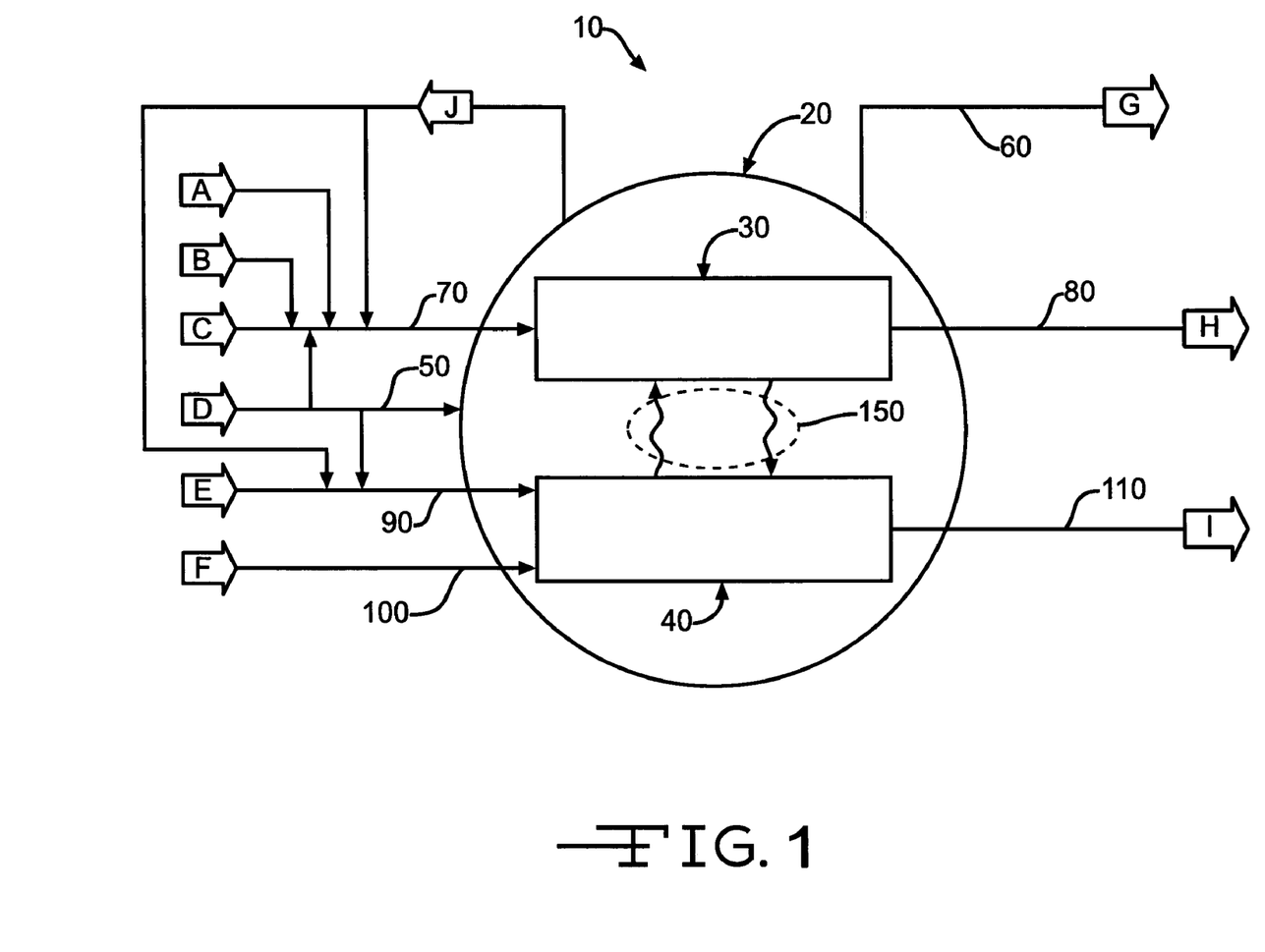
FIG. 1 is a schematic of an exemplary microchannel process according to the present invention.

The following reference indicators are provided as an aid to an understanding of the figures:
10 microchannel process
20 containment vessel
30 first microchannel process unit
40 second microchannel process unit
50 containment vessel inlet
60 containment vessel vent
70 first microchannel process unit inlet
80 first microchannel process unit outlet
90 first process unit inlet to second microchannel process unit
100 second process unit inlet to second microchannel process unit
110 second microchannel process unit outlet
150 process unit—process unit heat transfer
A first reactant material
B first catalyst activation material
C second reactant material
D pressurizing material
E third reactant material
F fourth reactant material
G vented/flared material
H first products material
I second products material
J purge material Reference to FIG. 1, an exemplary microchannel process 10, will assist in an understanding of the invention. At least one microchannel process unit 30, 40 of a design and construction suitable for the unit operation(s) of interest is at least partially contained within a containment vessel 20. While two microchannel process units 30, 40 are shown, one or a large plurality of process units 30, 40 may be included. For example, it is known in the microchannel art to construct a device which embodies hundreds or even thousands of individual reactors, oftentimes in a configuration which interleaves a plurality of unit operations. In this way, for example, a unit which processes an endothermic reaction may be placed in close contact with a unit which processes a combustion or exothermic reaction. More particularly, the first microchannel process unit 30 comprises a catalyzed endothermic SMR reaction and the optional second microchannel process unit 40 comprises an optionally catalyzed exothermic combustion operation. For optimal performance, the first microchannel process unit 30 and the second microchannel process unit 40 are placed in close proximity to promote the transfer of thermal energy 150 from one unit to another.

Piping and stream flows include a containment vessel inlet 50 via which pressurizing material D may be introduced into the containment vessel 20. The pressurizing material D may comprise any suitable material and generally a readily-available inert gas such as nitrogen is used. Depending upon the operation, however, steam or non-combustible or non-oxidizing material may be suitable as may reactive material. Compressor(s) (not shown) for boosting the pressure of the pressurizing material D may also be utilized. Finally, the pressurizing material D may be introduced to other regions of the microchannel process 10 via, for example, a first microchannel process inlet 70 to the first microchannel process unit 30 and the first inlet to the second microchannel process unit 90 to the second microchannel process unit 40.

Piping exiting the containment vessel 20 may include, nominally, a vent 60 through which vented or flared material G may flow. Purge material J may also exit the containment vessel 20 and be directed to the first microchannel process unit 30 through the first microchannel process inlet 70 and/or the second microchannel process unit 40 (via the first inlet to the second microchannel process unit 90 shown).

Piping and stream flow to and from the first microchannel process unit 30 will be suitable for the unit operation desired. As shown in FIG. 1, for example, in addition to the pressurization material D, a first reactant material A and a second reactant material C may be introduced into the first microchannel process unit 30 via the first microchannel process unit inlet 70. In the exemplary SMR operation, the first reactant material A would comprise steam and the second reactant material C natural gas or other mixture than contains methane. Optionally, a first catalyst activation material B, combined with, for example, nitrogen from pressurization material D, may be introduced into the first microchannel process unit 30 via the first microchannel process unit inlet 70. In the exemplary SMR operation utilizing a Group VIII-, e.g., nickel-, or preferably, a rhodium-based catalyst, the first catalyst activation material B comprises hydrogen. Provision may also be made for introducing a material J from the containment vessel 20, via the first microchannel inlet 70, to the first microchannel process unit 30 for, for example, purging. In the case of a shutdown, and particularly an emergency shutdown, the availability of an inventory of hot purge material J, is highly desirable. Damage from thermal shock may be minimized or avoided by purging with a purging material J that is at, or nearly at, the temperature of the at least one microchannel process unit 30, 40. Finally, first products material H may be withdrawn from the first microchannel process unit 30 via a first microchannel process unit outlet 80.

So, too, piping and stream flow to and from the optional (or additional) second microchannel process unit 40 will be suitable for the unit operation desired. As shown in FIG. 1, for example, in addition to the pressurization material D, a third reactant material E may be introduced into the second microchannel process unit 40 via the first inlet to the second microchannel process unit 90 and a fourth reactant material F via the second inlet to the second microchannel process unit 100. In the exemplary SMR operation, the second microchannel process unit 40 processes a combustion reaction unit operation. The third reactant material E comprises combustible fuel such as natural gas and the fourth reactant material F comprises an oxidizer such as air. As with the first microchannel process unit 30, provision may be made for introducing the material J from the containment vessel 20. Finally, a second product material I may be withdrawn via the second microchannel process unit outlet 110.

In the exemplary SMR operation, the first microchannel process unit 30 effects an endothermic reformation reaction unit operation and comprises at least one microchannel (not shown) and, optionally, a suitable catalyst (not shown). The second microchannel process unit 40 effects an exothermic combustion reaction unit operation by combining the third reactant material E (e.g., natural gas, hydrogen, or other suitable fuel) with the fourth reactant material F (e.g., air or other suitable oxidizer). Process unit—process unit heat transfer 150 enables the heat generated in the second microchannel process unit 40 to be utilized in the first microchannel process unit 30. The first product material H comprises a typical yield of 75 percent hydrogen, 15 percent carbon monoxide, and ten percent carbon dioxide. The second product material I comprises combustion products.

Cold startup of the microchannel process 10 begins (FIGS. 2 and 2A) with the standard preparation steps of inspecting all utilities, control equipment, and valve alignment followed by a full system inspection. (Exemplary plant parameters reflect a first microchannel process unit 30 performing SMR and a second microchannel process unit 40 performing combustion.) The containment vessel 20 is then pressurized with pressurizing material D, preferably with an inert such as nitrogen, and preferably to a standard plant supply pressure of, for example 90 psig. (While exemplary pressures of above-atmospheric are shown and discussed, it will be appreciated by those skilled in the art, that sub-atmospheric pressures may also be considered within the scope and spirit of the invention.) After checking for leaks from the containment vessel 20 using traditional methods (e.g., loss of pressure in the containment vessel 20 or pressure gain in either the first or second microchannel process unit 30, 40), the containment vessel 20 is next pressurized with pressurizing material D to a pressure higher than nominal working pressure, for example to 400 psig. The containment vessel 20 is again checked for leaks using traditional methods.

Figure 2:
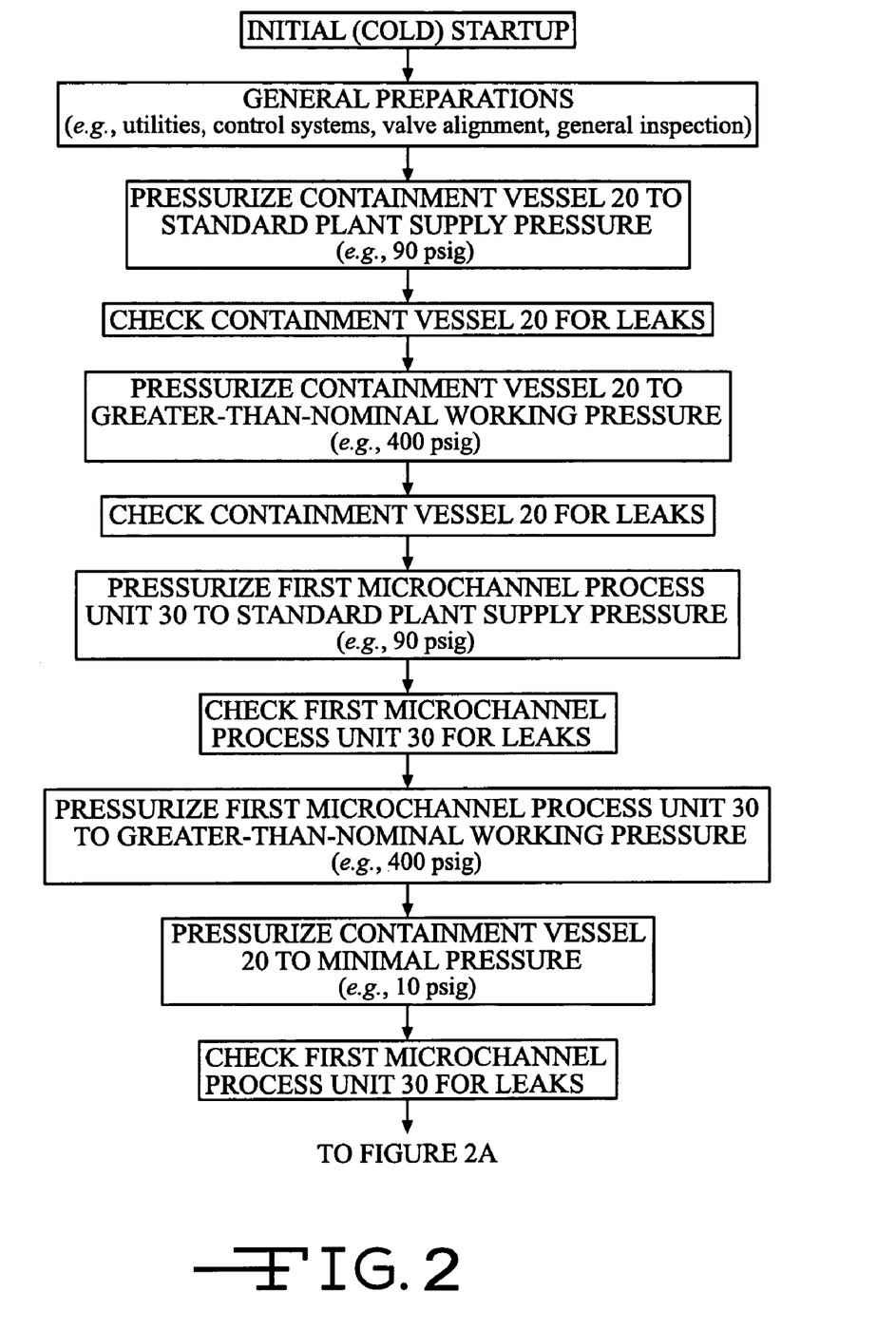
FIGS. 2 and 2A is a flow diagram of an exemplary microchannel process startup according to the present invention.
Figure 2A:
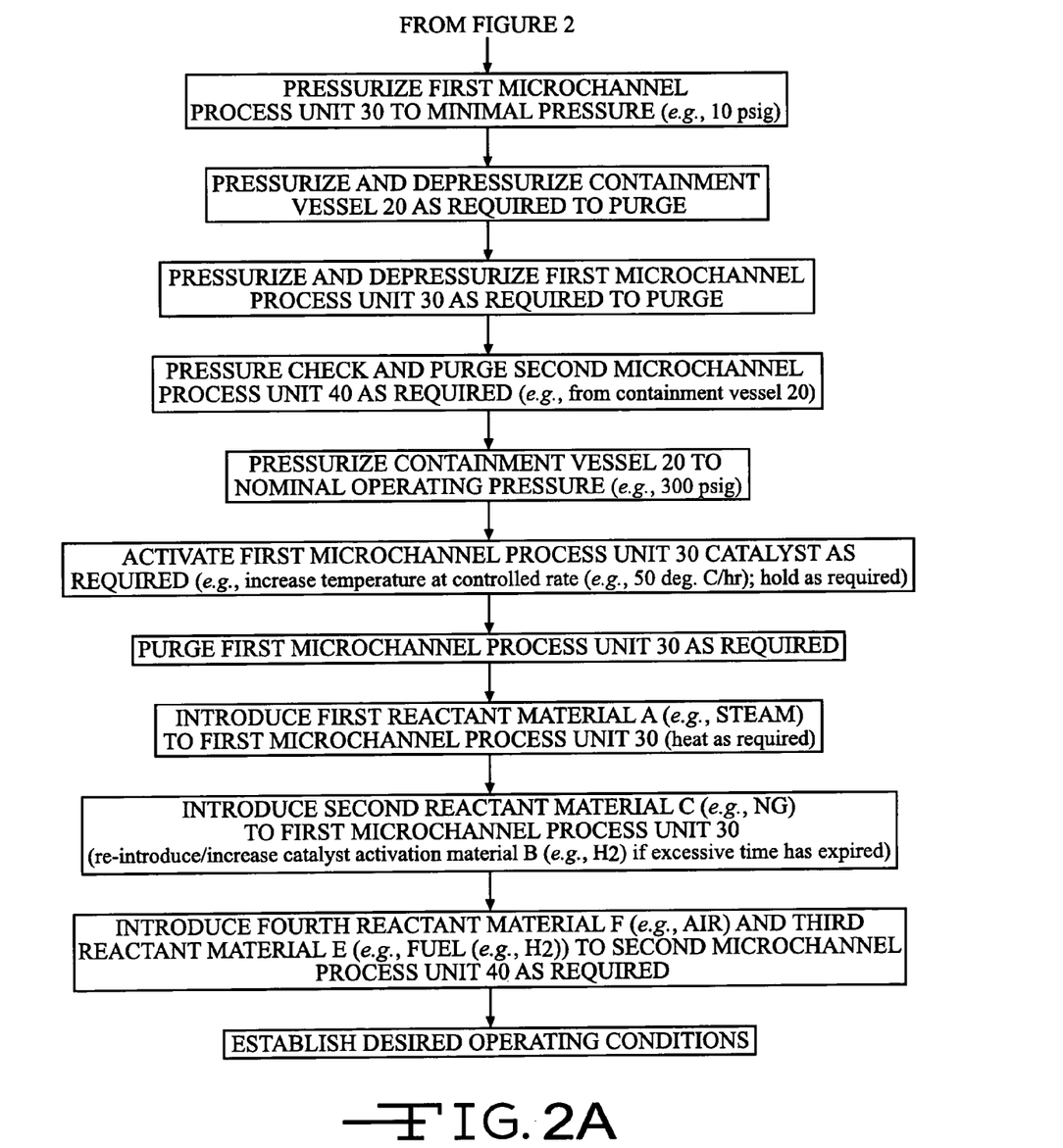

Next, the first microchannel process unit 30 is pressurized with pressurizing material D, preferably to a standard plant supply pressure. Preferably, the pressure in the containment vessel 20 is maintained at the higher (above nominal working pressure) pressure. Checks are made for leaks, particularly to the second microchannel process unit 40. The first microchannel process unit 30 is then pressurized with pressurizing material D to a pressure higher than nominal working pressure, for example to 400 psig, the pressure in the containment vessel is reduced to a minimal value, for example 10 psig, and the first microchannel process unit 30 checked for leaks into the containment vessel 20. Note that this reverse pressure differential may be tolerated by the first microchannel process unit 30 at lower temperatures. At higher temperatures, in the 650-1,000 deg. C. range, such a differential may not be tolerated in a microchannel unit. The first microchannel process unit 30 is then depressurized to a minimal value, for example 10 psig, through the first microchannel process unit outlet 80. If the pressurizing step for the first microchannel process unit 30 utilizes an inert such as nitrogen, the depressurizing step acts as a purge and reduces the oxygen content in the first microchannel process unit 30, depending upon the pressures utilized, from 21 percent to just over one percent. The same effect can be had in the containment vessel 20. Optionally, if required, the pressurization/depressurization steps may be repeated until an acceptable level of oxygen is achieved. The optional second microchannel process unit 40 is similarly pressured checked and purged as required. Following completion of the pressure checks, the containment vessel 20 is pressurized with pressurizing material D to its operating pressure of, for example 300 psig.

In the exemplary catalyzed SMR operation, for example, the catalyst may require an activation step. Suitable materials, for example pressurizing material D in the case of nitrogen and first catalyst activation material B (hydrogen, e.g.), are flowed over the catalyst in the first microchannel process unit 30. Concurrently, the catalyst may be heated at a controlled rate, preferably, in the case of an SMR, of 50 deg. C. per hour. Upon reaching a pre-established temperature, preferably about 300 deg. C., the catalyst is held at that temperature for a suitable length of time, preferably one hour. In the case of nitrogen and hydrogen, the hydrogen level is preferably controlled at or below ten percent.

Prior to actual startup of the first microchannel process unit 30, the first microchannel process unit 30 is purged as required. To startup the first microchannel process unit 30, the first reactant material A is introduced. In the case of the exemplary SMR operation, the first reactant material A comprises steam. When the flow of the first reactant material A is established and any desired pressure or temperature levels achieved, the second reactant material C is introduced into the first microchannel process unit 30. (In the case of SMR, the desired temperature level would be about 300 deg. C. Also, in the case of SMR, the second reactant material C comprises a methane-based material such as natural gas.) Since SMR is an endothermic reaction, the conversion of steam and methane is self-limiting without a heat source. Beginning an endothermic reaction in the first microchannel process unit 30 and then initiating an exothermic reaction in the second microchannel process unit 40 reduces the chances of a "hot spot" in the microchannel process 10 as the material in the first microchannel process unit 30 acts as a heat sink. Note that with a catalyzed SMR process and activated catalyst, excessive exposure to steam can at least partially deactivate the catalyst. Thus, if the addition of the second reactant material C (e.g., natural gas for SMR) is delayed, material should be added with the first reactant material A (e.g., catalyst activation material B (hydrogen) to steam for SMR).

To startup the optional second microchannel process unit 40, the fourth reactant material F is introduced. (Air or other oxidizer in an SMR case with a combustor.) The third reactant material E (e.g., hydrogen) is then introduced. Optionally, and preferably for an SMR, either the third reactant material E, the fourth reactant material F, or both are initially diluted with, for example, a pressurizing material D such as nitrogen. This provides the benefit of controlled heating of the first microchannel process unit 30. The temperature of the first microchannel process unit 30 is allowed, in a controlled manner (e.g., 50 deg. C./hour), to rise to operating conditions (e.g., 850 deg. C.). As thermal control may be critical in the microchannel environment, temperature increases are closely controlled. For example, introducing a high-thermal density material (e.g., methane) at the outset, may cause hot spots to form which may damage the integrity of the process units 30, 40. To overcome this problem, a low-thermal density material (e.g., hydrogen), preferably a dilute low-thermal density material, may be introduced as the third reactant material E. In the exemplary SMR case, the third reactant material comprises five percent hydrogen. As the temperature increases, the proportion of hydrogen is increased to, e.g., 15 percent. This allows a modest and easily-controlled temperature rise. Preferably, and at an appropriate time in the startup process, a high-thermal density material (e.g., methane), preferably a dilute high-thermal density material is introduced in place of the low-thermal density material. Again, in the exemplary SMR case, the third reactant material comprises five percent methane. As the temperature increases, the proportion of methane is increased and operating conditions established as required.

Importantly, presence of the containment vessel 20 operating as a thermal blanket over, for example, the second process unit 40, enables improved thermal control. Where the second process unit 40 comprises a catalyzed combustion unit operation, the catalyst may be required to function at a designed temperature of 700-900 deg. C. but may be required to be active at a much lower temperature for startup. Thus, the ability to raise the temperature of the second process unit 40 from ambient to, for example, 300 deg. C., enables greater catalyst design flexibility. Filling the containment vessel 20 with, for example, superheated steam, can achieve such temperatures. Additionally, during normal operation the pressurizing material D contained within the containment vessel 20 may function to reduce heat loss from the first process unit 30 and the optional second process unit 40 to ambient could be reduced, thus reducing any temperature gradient within the process units 30, 40 resulting in potentially improved overall performance. For example, with an exemplary endothermic reaction such as SMR, lower temperatures in peripheral microchannels could cause lower conversion in those channels.

Figure 3:
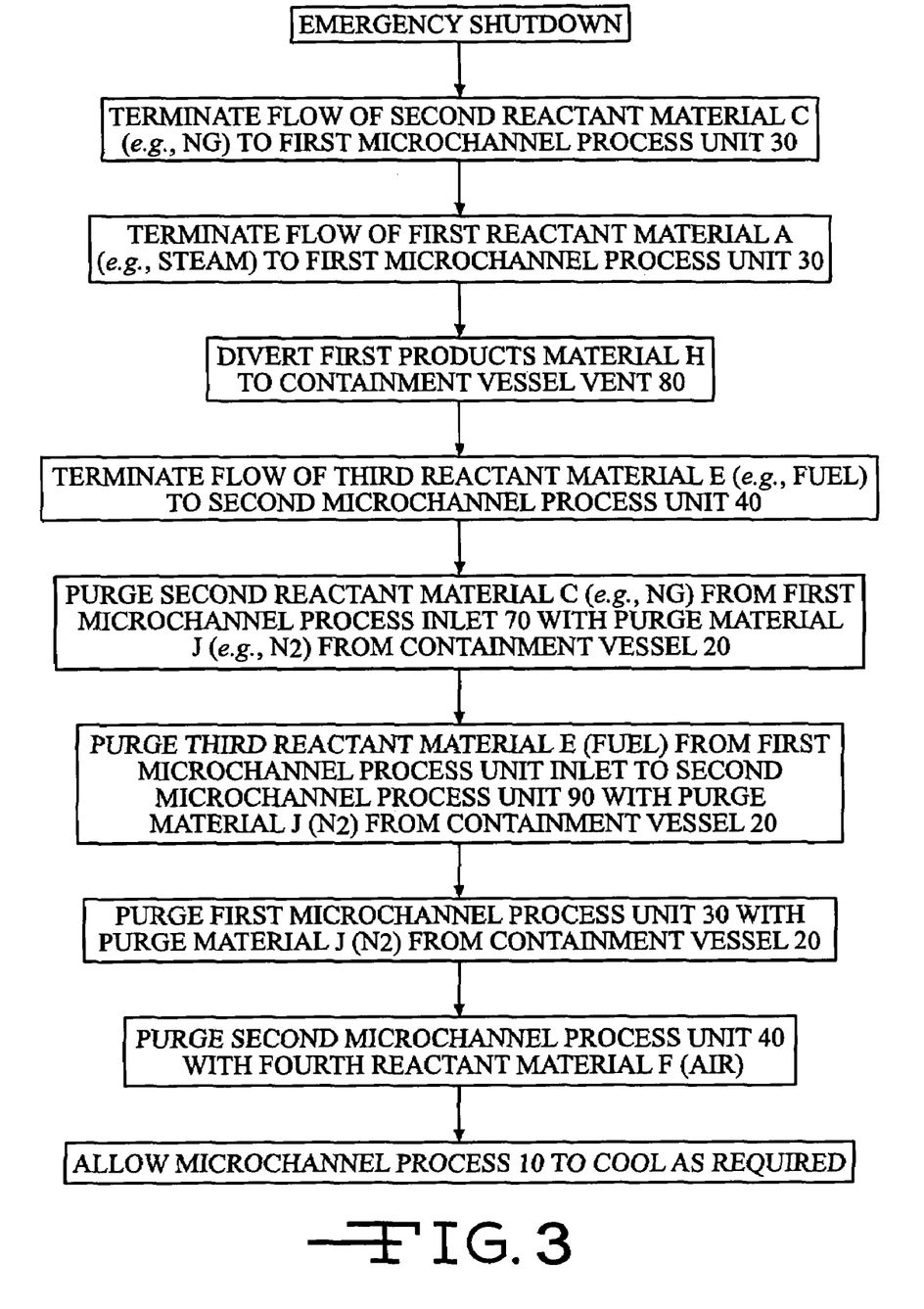
FIG. 3 is a flow diagram of an exemplary microchannel process emergency shutdown according to the present invention.

Shutdown, particularly an emergency shutdown (FIG. 3) which is performed in a short timeframe, must be accomplished not only quickly, but safely and with consideration to the process units 30, 40 and any catalysts employed. Initially, the flow of a reactant material to the first process unit 30 is reduced and stopped. In the SMR case, for example, this is the second reactant material C (e.g., natural gas). The flow of the first reactant material A to the first process unit 30 is also reduced and stopped. As will be appreciated by those skilled in the art, these steps may be done in either order or simultaneously. To avoid off-spec reactant material, the first products material H may be diverted (not shown) to a containment vessel vent 80. The optional second process unit 40 may be shutdown similarly by terminating flow of the third reactant material E to the second process unit 40. Preferably, the second reactant material C is purged from the first process inlet 70 with purge material J from the containment vessel 20. Additionally, the third reactant material E is likewise purged from the first process inlet 70. Finally, the process units 30, 40 are purged with purge material J from the containment vessel 20. This process provides an important thermal management benefit because it utilizes hot material from the containment vessel 20 which may supplied in sufficient quantities in a short timeframe. Again, as will be appreciated by those skilled in the art, these purge steps may be performed in varying orders and to varying feed lines to meet the unit operations specifics of the process.

Depending upon the conditions, particularly the thermal conditions, existing at the time of startup or restart, the startup process may be abbreviated. For example, the catalyst may be hot enough to work well (e.g., a palladium combustion catalyst would work above 500 deg. C. for combustion of methane, but would not have sufficient activity to ignite methane combustion below 400 deg. C.) without supplemental heating. Importantly, the process units 30, 40 may be hot enough to proceed with high temperature operation without creating undesirable hot spots.

Figure 4:
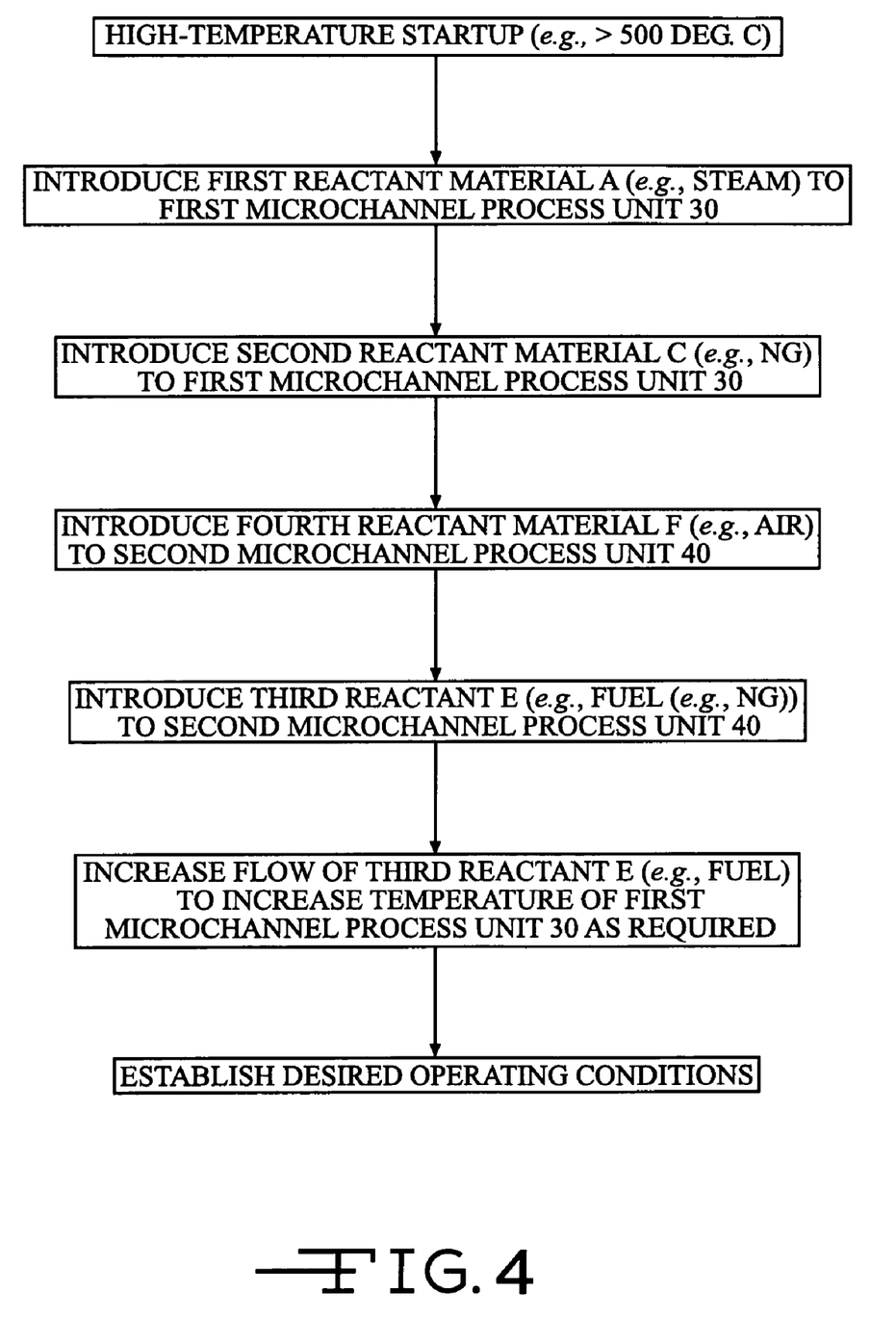
FIG. 4 is a flow diagram of an exemplary microchannel process high-temperature startup according to the present invention.

Turning now to FIG. 4, if the process units 30, 40 are above a threshold temperature (e.g., 500 deg. C. in an SMR operation), the first reactant material A and second reactant material C may be introduced to the first microchannel process unit 30 forthwith. If the second process unit 40 processes a combustion unit operation, it is generally desirable to purge any combustibles (e.g., hydrogen or methane) from the first process unit inlet to the second microchannel process unit 90 and the second microchannel process unit 40. Preferably, inert material such as the pressurizing material D (e.g., nitrogen) may be used. In the hot startup case shown in FIG. 4, high-thermal density fuel such as methane (third reactant E) may be introduced, albeit preferably in a dilute stream, to the second microchannel process 40. Flow of the third reactant E may then be increased to effect an increase in temperature of the first microchannel process unit 30 as required.

Figure 5:
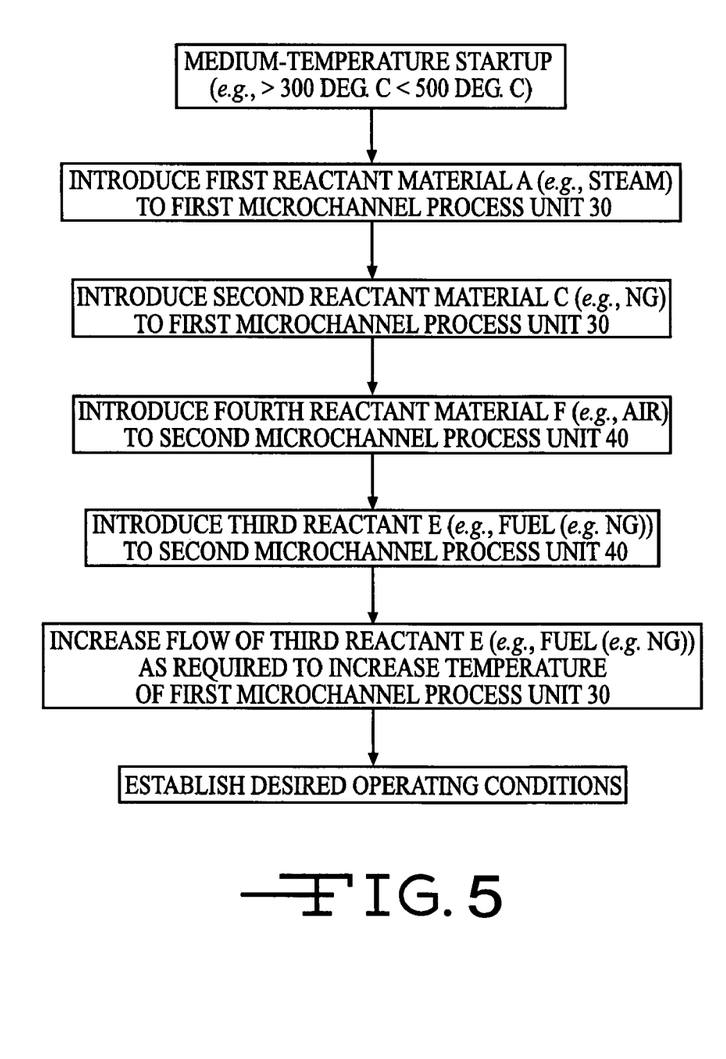
FIG. 5 is a flow diagram of an exemplary microchannel process medium-temperature startup according to the present invention.

FIG. 5 shows a mid-range temperature situation. In the exemplary SMR operation, the range is 300-500 deg. C. As shown, FIGS. 4 and 5 are identical. In the exemplary SMR case, however, there would be a difference. Where the hot startup case of FIG. 4 utilizes a third reactant E comprising dilute high-thermal density fuel (e.g., methane), the mid-range temperature case preferably uses a third reactant E comprising dilute low-thermal density fuel (e.g., hydrogen) initially, which is then gradually converted to high-thermal density fuel (e.g., methane) as required.

Figure 6:
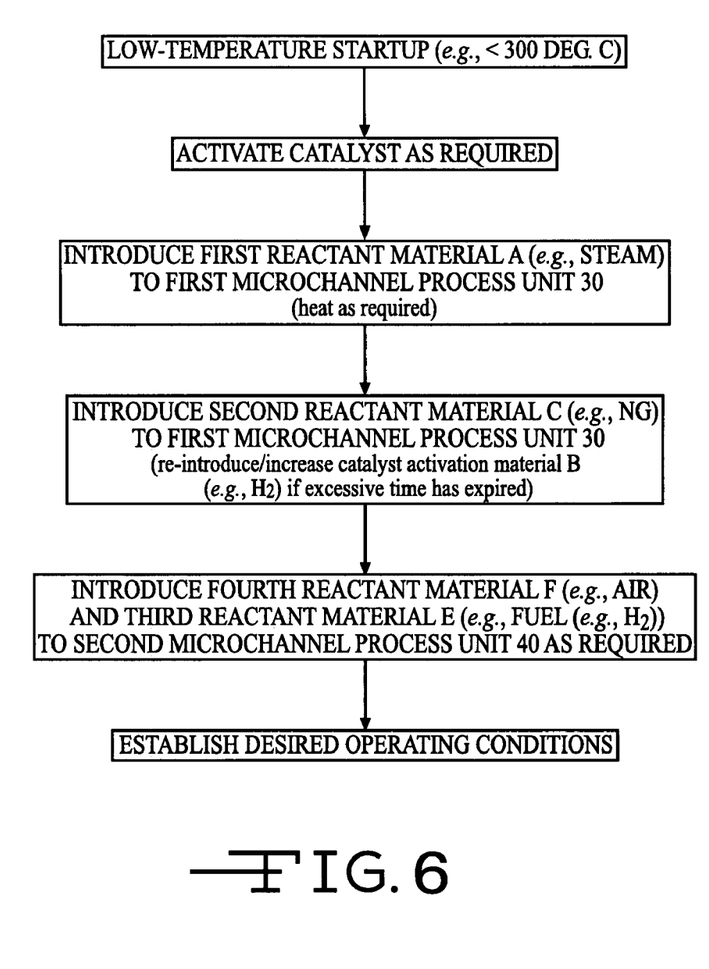
FIG. 6 is a flow diagram of an exemplary microchannel process low-temperature startup according to the present invention.

Finally, FIG. 6 shows a low-temperature situation. In the exemplary SMR operation, this is below 300 deg. C. and the startup procedure mimics the "Initial (Cold) Startup" illustrated in FIGS. 2 and 2A without the pressurization checks.

Following from the above description and invention summaries, it will be appreciated by those skilled in the art that, while the processes and methods described herein and illustrated constitute exemplary embodiments of the present invention, the invention is not limited to those precise embodiments and that changes and modifications may be made thereto without departing from the scope of the invention as defined by the claims. Likewise, it is to be understood that the invention is defined by the claims and it is not intended that any limitations or elements describing the exemplary embodiments set forth herein are to be incorporated into the claims unless explicitly recited in the claims themselves. Finally, it is to be understood that it is not necessary to meet any or all of the recited advantages or objects of the invention disclosed herein in order to fall within the scope of any claim, since the invention is defined by the claims and since inherent and/or unforeseen advantages of the present invention may exist even though they may not have been explicitly discussed herein.

We claim:

1. A method of starting up a microchannel process, comprising the steps of:
   (a) providing a first multi-planar microchannel process unit adapted to process a unit operation;
   (b) providing a containment vessel, the containment vessel at least partially containing the process unit;
   (c) establishing a first containment vessel pressure within the containment vessel;
   (d) sensing for leaks from the containment vessel;
   (e) establishing a first process unit pressure within the first process unit; and
   (f) sensing for leaks from the first process unit.

2. The method of claim 1, further comprising the step of:
   (a) initiating a unit operation within the first process unit.

3. The method of claim 1, wherein steps (c) through (f) are performed sequentially.

4. The method of claim 3, further comprising the step of:
   (a) following the step of sensing for leaks from the first process unit, initiating a unit operation within the first process unit.

5. The method of claim 1, wherein the step of sensing for leaks from the containment vessel comprises steps chosen from the list consisting of:
   (a) sensing for leaks from the containment vessel to an ambient surrounding;
   (b) sensing for leaks from the containment vessel to the first process unit; and
   (c) combinations thereof.

6. The method of claim 1, wherein the step of establishing the first pressure containment vessel pressure comprises:
   (a) introducing a fluid into the containment vessel, the fluid selected from the group consisting of: steam, inert, non-combustible, non-oxidizing, and mixtures thereof.

7. The method of claim 1, wherein the step of establishing the first process unit pressure comprises:
   (a) introducing a fluid into the first process unit, the fluid selected from the group consisting of: steam, inert, non-combustible, non-oxidizing, and mixtures thereof.

8. The method of claim 1, wherein the step of sensing for leaks from the first process unit comprises steps chosen from the list consisting of:
   (a) sensing for leaks from the process unit to an ambient surrounding;
   (b) sensing for leaks from the process unit to the containment vessel; and
   (c) combinations thereof.

9. The method of claim 1, further comprising the step of:
   (a) establishing a second containment vessel pressure within the containment vessel.

10. The method of claim 1, further comprising the steps of:
    (a) providing a catalyst within the first process unit; and
    (b) activating the catalyst.

11. The method of claim 1, further comprising the step of:
    (a) providing a second multi-planar microchannel process unit.

12. The method of claim 11, further comprising the step of:
    (a) at least partially containing the second process unit within the containment vessel.

13. The method of claim 12, further comprising the steps of:
    (a) initiating a first unit operation within the first process unit;
    (b) initiating a second unit operation within the second process unit.

14. The method of claim 13, further comprising the step of:
    (a) enabling the transfer of thermal energy between the first unit operation and the second unit operation.

15. A method of starting up a microchannel process, comprising the steps of:
    (a) providing a first multi-planar microchannel process unit adapted to process a first unit operation;
    (b) providing a containment vessel, the containment vessel at least partially containing the first process unit;
    (c) establishing a first containment vessel pressure within the containment vessel;
    (d) sensing for leaks of the first containment vessel pressure from the containment vessel;
    (e) establishing a second containment vessel pressure within the containment vessel;
    (f) sensing for leaks of the second containment vessel pressure from the containment vessel;
    (g) establishing a first process unit pressure within the first process unit;
    (h) sensing for leaks of the first process unit pressure from the first process unit;
    (i) establishing a second process unit pressure within the first process unit;
    (j) establishing a third containment vessel pressure within the containment vessel;
    (k) sensing for leaks of the second process unit process from the first process unit;
    (l) establishing a third process unit pressure within the first process unit;
    (m) establishing a fourth containment vessel pressure within the containment vessel; and
    (n) initiating the first unit operation within the first process unit.

16. The method of claim 15, wherein the first containment vessel pressure is a nominal plant pressure.

17. The method of claim 15, wherein the second containment vessel pressure is greater than a containment vessel operating pressure.

18. The method of claim 15, wherein the first process unit pressure is a nominal plant pressure.

19. The method of claim 15, wherein the second process unit pressure is greater than a first process unit operating pressure.

20. The method of claim 15, wherein the third containment vessel pressure is less than 90 psig.

21. The method of claim 15, wherein the fourth containment vessel pressure is a containment vessel operating pressure.

22. The method of claim 15, wherein the step of establishing a first process unit pressure comprises:
    (a) transferring a pressurization material from the containment vessel to the first process unit.

23. The method of claim 15, wherein a material from within the containment vessel is used to establish a pressure selected from the group consisting of: the first process unit pressure, the second process unit pressure, the third process unit pressure, and combinations thereof.

24. The method of claim 15, further including the step of:
    (a) establishing a first purging containment vessel pressure within the containment vessel; and
    (b) establishing a second purging containment vessel pressure, lower than the first purging containment vessel pressure, within the containment vessel, whereby an ambient material is at least partially purged from the containment vessel.

25. The method of claim 15, further including the step of:
(a) establishing a first purging process unit pressure within the first process unit; and
(b) establishing a second purging process unit pressure, lower than the first purging process unit pressure within the first process unit, whereby an ambient material is at least partially purged from the first process unit.

26. The method of claim 15, wherein the step of initiating the first unit operation within the first process unit comprises:
(a) providing a suitable catalyst within the first process unit; and
(b) activating the catalyst.

27. The method of claim 26, wherein the step of activating the catalyst comprises:
(a) introducing a suitable material to the first process unit.

28. The method of claim 27, wherein the suitable material is chosen from the group consisting of:
(a) inert, the inert chosen from the group consisting of: argon, nitrogen, helium, and mixtures thereof;
(b) reducer, the reducer chosen from the group consisting of hydrogen, carbon monoxide, ammonia, methane, and mixtures thereof;
(c) reactive, the reactive chosen from the group consisting of water, sulfur, halogen, ammonia, amine, and combinations thereof;
(d) oxidizer, the oxidizer chosen from the group consisting of oxygen and steam; and
(e) mixtures of:
(i) inert, reducer, and reactive; and
(ii) inert and oxidizer.

29. The method of claim 28, further comprising the step of:
(a) heating the suitable material.

30. The method of claim 26, further comprising the step of:
(a) introducing at least one reactant to the first process unit.

31. The method of claim 15, further comprising the steps of:
(a) providing a second multi-planar microchannel process unit adapted to process a second unit operation; and
(b) at least partially containing the second process unit within the containment vessel.

32. The method of claim 31, further comprising the steps of:
(a) establishing fourth process unit pressure within the second process unit;
(b) sensing for leaks of the fourth process unit pressure from the second process unit.

33. The method of claim 31, wherein the first unit operation is an endothermic reaction, and further comprising the steps of:
(a) enabling the transfer of thermal energy between the first unit operation and the second unit operation.

34. The method of claim 31, further comprising the steps of:
(a) introducing a combustible material to the second process unit; and
(b) introducing an oxidant material to the second process unit, whereby a combustion reaction proceeds within the second process unit.

35. The method of claim 34, further comprising the step of:
(a) enabling the transfer of thermal energy between the second process unit and the first process unit.

36. The method of claim 15, further comprising the step of:
(a) maintaining a differential between the fourth containment vessel pressure within the containment vessel and the third process unit pressure within the first process unit.

37. A method of starting up a microchannel process, comprising the steps of:
(a) providing a first microchannel process unit adapted to process a first unit operation;
(b) providing a second microchannel process unit adapted to process a second unit operation;
(c) placing the first process unit and the second process unit in thermal communication;
(d) introducing a first reactant to the first process unit;
(e) introducing a second reactant to the first process unit;
(f) introducing a third reactant to the second process unit; and
(g) introducing a fourth reactant to the second process unit.

38. The method of claim 37, further comprising the step of:
(a) providing a homogeneous catalyst.

39. The method of claim 37, wherein:
the first reactant is steam; and further comprising the steps of:
(a) providing a catalyst within the first process unit;
(b) activating the catalyst; and
(c) conditionally, if feeding the second reactant is not initiated within a time period of one hour (1), adding a diluent to the steam.

40. The method of claim 39, wherein the time period is ten (10) minutes.

41. The method of claim 39, wherein the diluent is hydrogen.

42. The method of claim 41, wherein the time period is ten (10) minutes.

43. The method of claim 37, wherein:
the first unit operation is an endothermic reaction between the first reactant and the second reactant;
the second unit operation is an exothermic reaction between the third reactant and the fourth reactant; and
the method of claim 37 further comprises the steps of:
(a) initiating a reaction in the first process unit;
(b) subsequently, initiating a reaction in the second process unit; and
(c) transferring thermal energy from the second unit operation to the first unit operation.

44. The method of claim 43, wherein:
the third reactant material comprises a low-thermal energy density material, the low-thermal energy density material comprising a diluent; and
the step of initiating a reaction in the second process unit further comprises:
(a) decreasing the proportion of the diluent in the third reactant material.

45. The method of claim 44, wherein the low-thermal density material comprises hydrogen.

46. The method of claim 45, wherein the diluent is chosen from the group consisting of: nitrogen, carbon dioxide, and steam.

47. The method of claim 44, further comprising the step of:
(a) replacing the low-thermal energy density material with a high-thermal energy density material.

48. The method of claim 47, wherein the high-thermal energy density material comprises methane.

49. The method of claim 43, wherein:
the third reactant material comprises a high-thermal energy density material.

50. The method of claim 49, wherein:
the third reactant material further comprises a diluent; and
the step of initiating a reaction in the second process unit further comprises:
(a) decreasing the proportion of diluent in the third reactant material.

51. The method of claim 43, wherein:
the first unit operation is a steam-methane reformation reaction; and
the second unit operation is a combustion reaction.

52. The method of claim 37, further comprising the steps of:
(a) providing a catalyst within the first process unit; and
(b) activating the catalyst.

53. A method of shutting down a microchannel process, comprising the steps of:
(a) providing a first microchannel process unit, the first process unit processing a first unit operation;
(b) discontinuing the flow of a second reactant to the first process unit;
(c) discontinuing the flow of a first reactant to the first process unit; and
(d) introducing a fluid to the first process unit, the fluid selected from the group consisting of: steam, inert, non-combustible, non-oxidizing, and mixtures thereof.

54. The method of claim 53, further comprising the steps of:
(a) providing a containment vessel, the containment vessel at least partially containing the first process unit; and
wherein the step of introducing a fluid to the first process unit comprises the step of:
(b) introducing a fluid from the containment vessel to the first process unit.

55. The method of claim 53, further comprising the steps of:
(a) providing a containment vessel, the containment vessel at least partially containing the first process unit; and
(b) introducing a fluid from the containment vessel to a second process unit.

56. A method of starting up a microchannel process, comprising the steps of:
(a) providing a first multi-planar microchannel process unit adapted to process a first unit operation;
(b) providing a second microchannel process unit adapted to process a second unit operation;
(c) providing a containment vessel, the containment vessel at least partially containing at least one process unit;
(d) introducing a first reactant material to the first process unit;
(e) introducing a second reactant material to the first process unit;
(f) introducing a fourth reactant material to the second process unit;
(g) introducing a third reactant material to the second process unit; and
(h) increasing the flow of the third reactant material, whereby the temperature of the first process unit increases.

57. The method of claim 56, wherein the third reactant material comprises a compound chosen from the list consisting of: methane and hydrogen.

58. A method of starting up a microchannel process, comprising the steps of:
(a) providing a microchannel process unit adapted to process a combustion operation;
(b) introducing a first reactant material to the process unit, the first reactant material comprising a combustible compound and a diluent;
(c) introducing a second reactant material to the process unit, the second reactant material comprising an oxidizing compound;
(d) initiating the combustion operation; and
(e) decreasing the proportion of diluent in the first reactant material.

59. The method of claim 58, wherein the combustible compound comprises a low-thermal density material.

60. The method of claim 59, wherein the low-thermal density material comprises hydrogen.

61. The method of claim 58, wherein the combustible compound comprises a high-thermal density material.

62. The method of claim 61, wherein the high-thermal density material comprises methane.

63. The method of claim 60, further comprising the steps of:
(a) substituting a high-thermal density material for at least a portion of the low-thermal density material.

* * * * *